United States Patent [19]

Saito et al.

[11] Patent Number: 4,897,379

[45] Date of Patent: Jan. 30, 1990

[54] N-[N$^\alpha$-(1(S)-CARBOXY-3-CYCLOHEXYL-PROPYL)-L-LYSYL]-N-CYCLOPENTYLG-LYCINE AS ANTIHYPERTENSIVES

[75] Inventors: Shizuo Saito; Motoshi Watanabe, both of Tokyo; Shuji Fukushima, Nagoya; Shinichi Matsui, Tokyo, all of Japan

[73] Assignee: Asahi Breweries Ltd., Tokyo, Japan

[21] Appl. No.: 172,565

[22] Filed: Mar. 24, 1988

[30] Foreign Application Priority Data

Mar. 24, 1987 [JP] Japan .................................. 62-67770

[51] Int. Cl.$^4$ ........................ A61K 37/02; C07K 5/06
[52] U.S. Cl. ..................................... 514/19; 530/316; 530/331; 562/500; 514/18
[58] Field of Search .................. 530/316, 331; 514/18, 514/19; 562/500

[56] References Cited

U.S. PATENT DOCUMENTS

| | | | |
|---|---|---|---|
| 3,947,575 | 3/1976 | Ondetti | 530/316 |
| 4,256,761 | 3/1981 | Suh et al. | 514/464 |
| 4,347,246 | 8/1982 | Suh et al. | 514/211 |
| 4,385,051 | 5/1983 | Oka et al. | 514/19 |
| 4,440,941 | 4/1984 | Suh et al. | 546/176 |
| 4,472,383 | 9/1984 | Oka et al. | 514/19 |
| 4,474,692 | 10/1984 | Oka et al. | 514/19 |
| 4,479,750 | 10/1984 | Menard et al. | 514/472 |
| 4,507,316 | 3/1985 | Youssefyeh et al. | 514/510 |
| 4,619,944 | 10/1986 | Youssefyeh et al. | 514/521 |
| 4,634,689 | 1/1987 | Witkowski et al. | 514/80 |
| 4,672,054 | 6/1987 | Kuprina et al. | 514/16 |
| 4,746,648 | 3/1988 | Wagnon et al. | 514/17 |

*Primary Examiner*—Lester L. Lee
*Attorney, Agent, or Firm*—Felfe & Lynch

[57] ABSTRACT

The invention relates to N-[N$^\alpha$-(1(S)-carboxy-3-cyclohexylpropyl)-L-lysyl]-N-cyclopentylglycine which is useful as antihypertensives.

2 Claims, No Drawings

N-[Nα-(1(S)-CARBOXY-3-CYCLOHEXYL-PROPYL)-L-LYSYL]-N-CYCLOPENTYLGLYCINE AS ANTIHYPERTENSIVES

BACKGROUND OF THE INVENTION

U.S. Pat. No. 4 374 826 discloses carboxyalkyl dipeptide derivatives and related compounds which are angiotensin converting enzyme inhibitors and accordingly useful as antihypertensives. U.S. Pat. Nos. 4 472 384 and 4 558 037 disclose mixture of carboxyalkyl dipeptide derivatives with compounds having different pharmacological actions. European Pat. Appln. Publication No. 51 391 discloses another compounds which are angiotensin converting enzyme inhibitors.

SUMMARY OF THE INVENTION

The invention in its broad aspects relates to N-[Nα-(1(S)-carboxy-3-cyclohexylpropyl)-L-lysyl]-N-cyclopentylglycine and derivatives thereof which are converting enzyme inhibitors and as useful antihypertensives.

The compounds of the invention can be produced by one or more of the methods shown as follows:

As is evident to those skilled in the art and as shown in the Examples, reactive groups not involved in the condensations, such as amino, carboxy, etc., may be protected by standard methods in peptide chemistry prior to the coupling reactions and subsequently deprotected to obtain the desired products.

Method 1

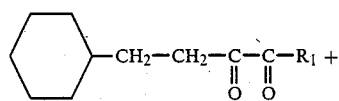

2

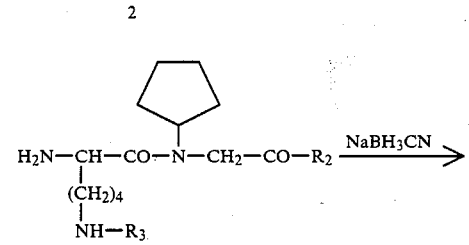

3

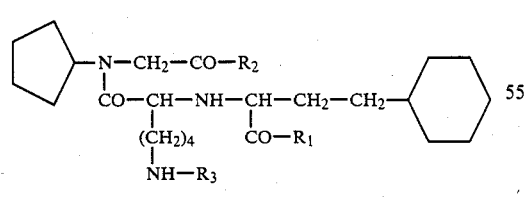

1

Keto acid (or its ester) 2 is condensed with dipeptide derivative 3 under optimally near neutral condition in aqueous solution, or in suitable solvent (for instance alcohol) in the presence of sodium cyanoborohydride to obtain 1. Alternatively the intermediate Schiff base is catalytically reduced by hydrogen concretely in the presence of palladium black or Raney nickel to obtain product 1. The ratio of diasteromeric products formed may be altered by choise of catalyst.

If $R_1$ and $R_2$ are carboxy protecting groups such as alkoxy or benzyloxy or the like, they can be converted by well-known methods such as hydrolysis or hydrogenation to 1, where $R_1$ and/or $R_2$ are hydroxy. This is applicable to the following methods where the above groups exist.

Alternativery lysine derivative 4 can be condensed with 2 under the same conditions to yield amino acid derivative 5.

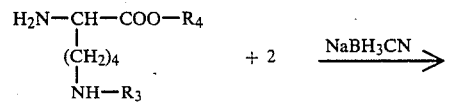

4

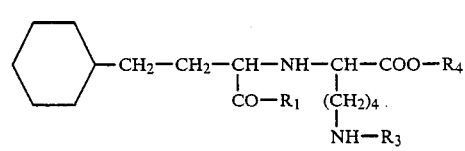

5

The thus obtained derivative 5, where in $R_4$ is protective group, may be converted to derivative 5, wherein $R_4$ is hydrogen, by removing the $R_4$ protective group. The fully protected derivative are separated by fractional crystallization, or silica gel, chromatography to yield each isomer.

Next, the amino acid derivative 6 is coupled with 5 (wherein $R_4$ is hydrogen) by well-known methods to yield 1.

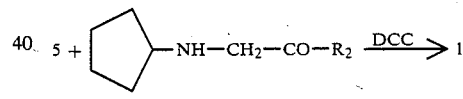

6

(DCC = dicyclohexylcarbodiimide)

Condensing agents useful in this synthetic method are those such as diethyl cyanophosphate, dicyclohexylcarbodiimide (DCC) or water-soluble carbodiimide (WSCI) and the like. And, 5 may be also activated as active esters derived from 1-hydroxybenzotriazole.

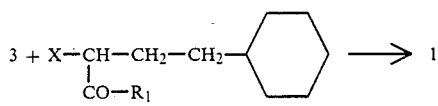

7

The dipeptide derivative 3 is alkylated with the proper α-haloacid (or its ester) under basic conditions in aqueous solution or an organic solvent. X is chlorine, bromine or iodine.

Alternatively, the synthesis can be carried out in a stepwise fashion.

4+7→5

5+6→1

That is, the lysine derivative 4 is alkylated by the α-haloacid (or its ester) 7 under basic conditions to obtain 5. Next, 5 is condensed by the general method as shown in Method 1 with the amino acid derivative 6 to obtain 1.

Reductive cleavage of a benzyl ester 1 (where $R_2$ is alkoxy and $R^1$ is benzyloxy) yields compounds of Formula 1 wherein $R_1$ is hydroxy and $R_2$ is alkoxy, and where $R_2$ benzyloxy and $R_1$ is alkoxy, yields compounds of Formula 1 wherein $R_2$ is hydroxy and $R_1$ is alkoxy.

The starting materials which are required for the above mentioned methods are well-known in the literature, or can be made by known methods from known starting materials.

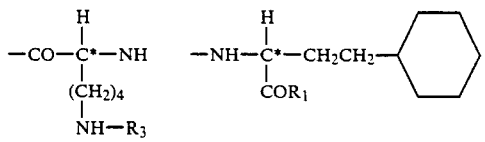

In the above partial structures of products shown as general Formula 1, the carbon atoms to which * is attached may be asymmetric. Accordingly, the compounds exist in diastereomeric forms or in mixtures thereof. The above described syntheses can utilize racemates, enantiomers or diastereomers as starting materials. When diastereomeric products result from the synthetic procedures, intermediate products may be included therein. The diastereomeric products can be separated from the mixture, at the most preferable separation stage by conventional chromatographic or fractional crystallization methods. The above mentioned partial structures of the products shown as Formula 1 are generally preferred in the S-configuration.

The compounds of this invention form salts with various inorganic and organic acids and bases. Such salts include ammonium salts, alkali metal salts such as sodium and potassium salts, alkaline earth metal salts such as calcium and magnesium salts, dicyclohexylamine salts and the like. Salts with organic and inorganic acids such as HCl, HBr, $H_2SO_4$, $H_2PO_4$, methane-sulfonic, toluensulfonic, maleic, fumaric, camphorsulfonic acids and the like are preferred. The non-toxic physiologically acceptable salts are preferred, although other salts are also useful.

The salts may be formed by conventional means such as by reacting the free acid or free forms of the product with one or more equivalents of the appropriate base or acid in a solvent for instance (medium in which the salt is insoluble), or in a solvent such as water which is then removed in vacuo. Otherwise, it is possible to exchange the cation of an salt on a suitable ion exchange resin for another-cation.

The compounds of this invention inhibit angiotensin converting enzyme and thus block formation of angiotensin II, and further prevent degradation of bradykinin by said enzyme, whereby blood-pressure can be lowered. As the such effective, well-known and similar medicines there can be enumerated Enalapril (manufactured by Merck & Co.), Lisinopril (manufactured by Merck & Co.) and CV-3317 (manufactured by Takeda Chemical Industries Ltd.). According to their comparative biological activity test results (Nature, vol. 288, page 280, (1980) and Chem. Pharm. Bull., vol. 34, page 1128 (1986)), the strength of activity is in order of Lisinopril>Enalapril>CV-3317. It has been found therefrom that CV-3317, namely the N-substituted glycine product of Enalapril, is rather lowered in activity, while the compound of this invention, as shown in the following table is more than 10 times stronger in activity than Lisinopril having the most strong activity.

TABLE $$R_1-COCHNHCHCH_2CH_2-R_2$$
$$\underset{NH_2}{\underset{|}{(CH_2)_4}}$$
with COOH on the first carbon

| $R_1$ | $R_2$ | $IC_{50}(M)$ |
|---|---|---|
| pyrrolidine-N, 2-COOH | phenyl | $1.1 \times 10^{-9}$ |
| cyclopentyl-NCH$_2$COOH | cyclohexyl | $1.0 \times 10^{-10}$ |

$IC_{50}(M)$ = Concentration inhibiting 50% of the activity of rabbit lung ACE was determined by the method of Friedland and Silverstein.

The compounds according to this invention have effective and considerably durable antihypertensive actions for various hypertensive model animals (hypertension spontaneous-suffered rats, normal rats attached by angiotensin I, high resin rats and the like), so that those compounds are useful as medicines to be used for the abovementioned purposes.

As stated previously, the compounds of this invention are in the S-configuration.

Accordingly, the compounds of this invention are useful for medical treatement of renovascular, malignant and essential hypertention, congestive heart failure, eye internal pressure exasperation and glaucoma.

The angiotensin converting enzyme inhibitors of the present invention may be used for mammals such as monkey, dog, cat, rat, human and the like. The compound of the present invention favorably may be blended in pharmaceutical preparations in the conventional manner. These compounds are made to take the common dosage form such as capsule, tablet, sugar-coating tablets, granule, solution, syrup, ointment, emulsion and the like and/or the depo form. The active substances may also exist in the microcapsulated form according to circumstances. The compound of the present invention may contain acceptable organic or inorganic auxiliary ingredients such, for instance, as granule-forming agents, adhesives and binder, lubricants, suspending agents, resolvent, antibiotics, humectant and preservatives.

In case where our compound is applied by parenteral, peroral and topical applications, about 0.5 to 50 mg is dosed 1 to 3 times per day. The topically used preparation may contain our compounds in an amount of 0.001 to 5 wt. %, and its dosage may be changed depending upon the condition of sickness, the weight of a patient and other factors recognized by a doctor.

The compound of the present invention may be used together with other diuretics or antihypertensives. As diuretics there may be enumerated those such, for instance, as hydrochlorothiazide, furosemide and the like.

As antihypertensives, there is used beta-blocker such as propranolol, thymolol, methyldopa and the like.

Auxiliary ingredients which may be mixed with tablets, capsules or minute glanules and the like are shown as follows, namely binder such as traganth, gum arabic, corn starch and gelatin excipient such as micro-crystal cellulose: swelling agents such as corn starch, pregelatinized starch, alginic acid and the like: lubricants such as magnesium stearate and the like: sweetening agents such as sucrose, lactose, saccharin and the like: and flavor such as peppermint, oil of wintergreen and cherry. When the unit preparation form of medicines is capsule, the above-mentioned type of materials may further contain liquid carriers such as fatty oil and the like. Various other materials may be present as coatings or to otherwise modify the physical form of the dosage unit. For instance, tablets may be coated with shellac, sugar or both. A syrup or elixir may contain active compounds; sweeting agents such as sucrose and the like, preservatives such as methyl and propylparaben; coloring matters; and a flavoring agent such as cherry and orange.

The sterile composite for injection may be prescribed according to conventional medical preparation by dissolving or suspending the active substance in the vehicle such as injectable water, a naturally occurring vegetable oil such as sesame oil, coconut oil, peanut oil, cottonseed oil and the like or in the synthetic fatty vehicle such as ethyl oleate or the like. Buffering agents, preservatives, antioxidants and the like can be added to the sterile composite as required.

Referring to the suppository, cacao butter and witepsol are used as bases, and carbowax is used as hydrophilic base. Said suppository may contain surface active agents, coloring agents, antioxidants.

The sterile composite used locally in eyes is prescribed in combination with the pharmaceutically acceptable carrier substance such, for instance, as aqueous methylcellulose. This combination may be practiced in the form of suspension, solution, ointment, emulsion or opthalmological insertion. This sterile composite may be prepared in the combination with such a compound as benzalkonium chloride having a preservative action.

The following example is illustrative of the invention and constitutes especially preferred embodiments.

EXAMPLE

N-[N$^\alpha$-(1(S)-carboxy-3-cyclohexylpropyl)-L-lysyl]-N-cyclopentylglycine (a) Preparation of N$^\epsilon$-benzyloxycarbonyl-L-lysine tert-butyl ester oxalate Liquid isobutene(25 ml) was added to a solution of N$^\epsilon$-benzyloxycarbonyl-L-lysine(3.6 g) in a mixture of dioxane(25 ml) and concentrated sulfulic acid(2.5 ml) in a 500 ml.pressure bottle, and the mixture was shaken mechanically at room temperature for 4 hr. The solution was poured immediately into a cold mixture of ether(200 ml) and 1N sodium hydroxide(125 ml), and the aqueous phase was washed well with ether. The ether solution was dried over sodium sulfate and evaporated under vacuum to about 5 ml. This was diluted with ether(10 ml). Addition of oxalic acid(2.3 g) in ether(15 ml) gave the crystalline oxalate(3.6 g).

TLC, Rf=0.65 (Developing solvent; n-buthanol:acetic acid:water=4:1:2; A, Detection; ninhydrin).

(b) Preparation of N-cyclopentylglycine tert-butyl ester

Sodium cyanoborohydride(1.9 g) was added portionwise to a stirred mixture of cyclopentanone(2.1 g), glycine tert-butyl ester hydrochloride(5.0 g), water(12 ml) and methanol(25 ml) during 15 min at water-bath temperature. The resulting mixture was stirred for 4 hr, diluted with 20% H$_3$PO$_4$(40 ml) and water(20 ml), and extracted with ether(80 ml). The aqueous layer was made alkaline(pH 10) with 20% NaOH and extracted with CHCl$_3$(50 ml). The extract was dried(Na$_2$SO$_4$) and concentrated in vacuo to give an oily residue, which was purified by silica gel column chromatography(ethyl acetate:hexane=3:1) to yield N-cyclopentylglycine tert-butyl ester(4.5 g) as a pale yellow oil.

TLC, Rf=0.55 (Developing solvent; ethyl acetate:n-hexane=3:1, Detection; peptide reagent).

(c) Preparation of N$^\alpha$-[1(S)-ethoxycarbonyl-3-cyclohexylpropyl]-N$^\epsilon$-benzyloxycarbonyl-L-lysine tert-butyl ester A mixture of L-Lys(Z)-OBu$^t$.oxalate(25.0 g) [obtain by step a)], sodium acetate(9.6 g), acetic acid(7.0 g), ethyl 2-oxo-4-cyclohexylbutylate(25.0 g) [prepared according to Chem. Pharm. Bull., 34, 1128 (1986)] and ethanol(150 ml) was stirred for 30 min, and then a solution of sodium cyanoborohydride(7.4 g) in ethanol(100 ml) was added dropwise to the mixture over 5 hr. After being stirred overnight, the mixture was diluted with saturated aqueous ammonium chloride solution(700 ml) and extracted with ethyl acetate (300ml×3). The extract was dried(MgSO$_4$) and evaporated in vacuo to give an oily residue, which was dissolved in diethyl ether(70 ml) containing oxalic acid(6.0 g). The resulting solution was diluted with petroleum ether(350 ml) and the supernatant layer was removed by decantation. The precipitate was neutralized with sodium bicarbonate(excess) and extracted with ethyl acetate. The extract was dried(MgSO$_4$) and evaporated in vacuo to give an oily residue, which was purified by column chromatography on silica gel using hexane-ethyl acetate(5:1) as an eluent. Evaporation of the first fraction afforded N$^\alpha$-[1(R)-ethoxycarbonyl-3cyclohexylpropyl]-N$^\epsilon$-benzyloxycarbonyl-L-lysine tertbutyl ester(13.8 g) as a colorless oil.

TLC, Rf=0.56 (Developing solvent; n-hexane:ethyl acetate=2:1, Detection; peptide reagent).

N$^\alpha$-[1(S)-ethoxycarbonyl-3-cyclohexylpropyl]-N$^\epsilon$-benzyloxycarbonyl-L-lysine tert-butyl ester was obtained from the subsequent fraction (8.1 g) as a colorless oil.

TLC, Rf=0.47 (Developing solvent; n-hexane:ethyl acetate=2:1, Detection; peptide reagent).

(d) Preparation of N$^\alpha$-[-1(S)-ethoxycarbonyl-3-cyclohexylpropyl]-N$^\epsilon$-benzyloxycarbonyl-L-lysine hydrochloride A solution of a colorless oil(8.0 g), obtained by step c), in HCl-AcOEt(3.6N, 80 ml) was allowed to stand for 4 hr. After evaporation of solvent, the residue was crystallized from diethyl ether(200 ml) to give N$^\alpha$-[1(S)-ethoxycarbonyl-3-cyclohexylpropyl]-N$^\epsilon$-benzyloxycarbonyl-L-lysine hydrochloride(6.0 g) as colorless needles.

TLC, Rf=0.53 (Developing solvent; benzene: methanol=4:1, Detection; peptide reagent).

(e) N-[N$^\alpha$-[1(S)-ethoxycarbonyl-3-cyclohexylpropyl]-N$^\epsilon$-benzyloxycarbonyl-L-lysyl]-N-cyclopentylglycine tert-butyl ester A solution of diethylphosphorocyanidate(3.8 g) in diethylformamide(DMF 80 ml) was added dropwise to a stirred mixture of a colorless needles(6.0 g), obtained by step (d), N-cyclopentylglycine tert-butyl ester(3.5 g), obtained by step (b), and DMF(150 ml). When the addition was complete, a solution of triethylamine(3.0 g) in DMF(20 ml) was added to the mixture. After being stirred for 1 hr, the mixture was diluted with water(1500 ml) and extracted with ethyl acetate(3000 ml). The extract was washed with 10% H$_3$PO$_4$(800ml×2), 1N NaOH(320 ml) and water successively, dried(Na$_2$SO$_4$) and evaporated in vacuo to give an oil residue, which was purified by silica gel column chromatography(hexane-ethyl acetate=1:1) to yield N-[N$^\alpha$-[1(S)-ethoxycarbonyl-3-cyclohexylpropyl]-N$^\epsilon$-benzyloxycarbonyl-L-lysyl]-N-cyclopentylglycine tert-butyl ester(5.5 g) as a colorless oil.

TLC, Rf=0.58 (Developing solvent; n-hexane:ethyl acetate=1:1, Detection; peptide reagent).

(f) N-[N$^\alpha$-[1(S)-ethoxycarbonyl-3-cyclohexylpropyl]-L-lysyl]-N-cyclopentylglycine dihydrobromide.

A 25% HBr-AcOH solution(20 ml) was added to a solution of a colorless oil(5.4 g), obtained by step (e), in acetic acid(20 ml). The resulting mixture was stirred for 1 hr and diluted with diethyl ether(1500 ml) to deposit colorless crystals of the dihydrobromide which were collected by filtration to give N-[N$^\alpha$-[1(S)-ethoxycarbonyl-3-cyclohexylpropyl]-L-lysyl]-N-cyclopentylglycine dihydrobromide(4.7 g).

TLC, Rf=0.48 (Developing solvent; A, Detection; ninhydrin).

(g) N-[N$^\alpha$-(1(S)-carboxy-3-cyclohexylpropyl)-L-lysyl]-N-cyclopentylglycine A mixture of a monoacid(4.6 g), obtained by step f), and 1N NaOH(150 ml) was allowed to stand for 1 hr, and thereafter absorbed with cation ion-exchange resin DOWEX 50W-X2. Elution with 2% aqueous pyridine and freeze-drying gave the desired N-[N$^{60}$-(1(S)-carboxy-3-cyclohexylpropyl)-L-lysyl]-N-cyclopentylglycine(3.0 g) as a colorless powder.

TLC, Rf=0.34 (Developing solvent; A, Detection; ninhydrin).

We claim:
1. N-[N$^\alpha$-(1(S)-carboxy-3-cyclohexylpropyl)-L-lysyl]-N-cyclpentylglycine and pharmaceutically acceptable salts thereof.
2. A medical composition useful for treating hypertensions which contains N-[N$^\alpha$-(1(S)-carboxy-3-cyclohexylpropyl)-L-lysyl]-N-cyclopentylglycine or its pharmaceutically acceptable salt in a medically effective amount.

* * * * *

UNITED STATES PATENT AND TRADEMARK OFFICE
CERTIFICATE OF CORRECTION

PATENT NO. : 4,897,379
DATED : January 30, 1990
INVENTOR(S) : Saito, et al.

It is certified that error appears in the above-identified patent and that said Letters Patent is hereby corrected as shown below:

COLUMN 8:

CLAIM 1, line 2: change "cyclpentylglycine" to -- cyclopentylglycine

CLAIM 2, line 1: change "medical" to -- pharmaceutical --.
       line 5: after "amount" add -- and a pharmaceutically acceptable carrier --.

Signed and Sealed this

First Day of October, 1991

Attest:

HARRY F. MANBECK, JR.

Attesting Officer     Commissioner of Patents and Trademarks